United States Patent
Drummond et al.

(10) Patent No.: US 6,816,567 B2
(45) Date of Patent: Nov. 9, 2004

(54) SYSTEM AND METHOD FOR ACQUIRING X-RAY DATA

(75) Inventors: Danielle Drummond, Wauwatosa, WI (US); Jiang Hsieh, Brookfield, WI (US); Ting-Yim Lee, London (CA); Robert Franklin Senzig, Caledonia, WI (US); Robert James Young, Wauwatosa, WI (US)

(73) Assignee: GE Medical System Global Technology Company, LLC, Waukesha, WI (US)

( * ) Notice: Subject to any disclaimer, the term of this patent is extended or adjusted under 35 U.S.C. 154(b) by 239 days.

(21) Appl. No.: 10/064,440

(22) Filed: Jul. 15, 2002

(65) Prior Publication Data

US 2004/0008819 A1 Jan. 15, 2004

(51) Int. Cl.[7] .................................................. A61B 6/00
(52) U.S. Cl. ............................ 378/16; 378/901; 378/19
(58) Field of Search ................................ 378/16, 15, 4, 378/19, 901, 109, 113

(56) References Cited

U.S. PATENT DOCUMENTS

| 4,392,096 A | | 7/1983 | Grajewski et al. .......... 318/625 |
| 5,485,494 A | * | 1/1996 | Williams et al. ............... 378/16 |
| 5,625,662 A | * | 4/1997 | Toth et al. ..................... 378/16 |
| 5,668,845 A | * | 9/1997 | Migita ............................ 378/4 |
| 6,198,789 B1 | | 3/2001 | Dafni ............................. 378/8 |
| 6,574,229 B1 | * | 6/2003 | Takahashi et al. .......... 370/400 |

FOREIGN PATENT DOCUMENTS

| EP | 0 405 862 A1 | 6/1990 |
| EP | 0 691 104 B1 | 10/1991 |

* cited by examiner

Primary Examiner—David V. Bruce
Assistant Examiner—Irakli Kiknadze
(74) Attorney, Agent, or Firm—Cantor Colburn LLP (57) ABSTRACT

A system and method of acquiring x-ray data, comprising: acquiring a series of x-ray data for generating at least one x-ray image using an x-ray detector to receive x-ray beams from an x-ray source, wherein an object being imaged is displaced along an axis, the axis extending perpendicularly through a plane defined by the x-ray beams, wherein the displacement occurs at, at least one of a constant, accelerating, and decelerating rates; varying the rate of displacement thus enabling the x-ray detector to acquire data for at least one x-ray image during accelerating or decelerating displacement; and employing current modulation.

25 Claims, 7 Drawing Sheets

FIG. 8

SYSTEM AND METHOD FOR ACQUIRING X-RAY DATA

BACKGROUND OF INVENTION

This invention relates generally to imaging systems and specifically to a system and method for acquiring x-ray data.

In CT imaging systems, an x-ray source projects a fan-shaped beam that is collimated to lie within an X-Y plane, generally referred to as an "imaging plane", of a Cartesian coordinate system toward an array of radiation detectors, wherein each radiation detector includes a detector element disposed within the CT system so as to receive this fan-shaped beam. An object, such as a patient, is disposed between the x-ray source and the radiation detector array so as to lie within the imaging plane and thus is subjected to the x-ray beam, which passes through the object. As the x-ray beam passes through the object, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam intensity at the detector element location. These electrical signals are referred to as x-ray attenuation measurements or x-ray images.

The x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object. In CT systems that employ a single detector array, the slice thickness is controlled and determined by the width of the collimator, while in CT systems that employ a multiple detector array, the slice thickness is controlled and determined by summing the contributions of a plurality of detector sub-units and by physically moving the collimator to the outer edges of each slice.

A goal of perfusion exams, such as those performed using a CT scanner, is to obtain a series of images for a given location within an allotted amount of time and within given sampling frequency. As a result, maximum spatial coverage is a factor of and limited by allotted time. Moreover, repetitive scanning of separate locations requiring additional time is necessary to image larger spatial areas. An embodiment of the present invention provides for a system and method of acquiring x-ray data.

BRIEF DESCRIPTION OF DRAWINGS

Referring to the exemplary drawings wherein elements are numbered alike in the several Figures.

DETAILED DESCRIPTION

While an exemplary system and method for acquiring x-ray data is disclosed herein with reference to a computed tomography (CT) imaging system, it should be understood that the method and system of the present invention may be applied to other imaging systems, such as Magnetic Resonance Imaging (MRI) systems.

A feature of an embodiment of the present invention is to repeatedly cover the same area over a short amount of time, thus extending the scan coverage over time beyond what is obtainable using cine or axial scanning. Another feature is to use bi-directional scanning to acquire time course images at given locations. Another feature is to increase coverage for a given scan time during a helical pass, without increasing table speed or rotation speed.

An embodiment of the present invention decreases the average time between passes/image sets for bi-directional helical protocols, thereby reducing the overall scan time for a given coverage, thus allotting for perfusion imaging of larger organs of the body that require larger axial coverage. Perfusion imaging requires continuous coverage of locations over time. Also, large organs such as the liver have time constraint for maintaining contrast enhancement, in addition to requiring large axial scan ranges. An embodiment of the present invention allows for faster, more complete coverage of large areas, with minimal time delays between acquisitions.

Figure 1:
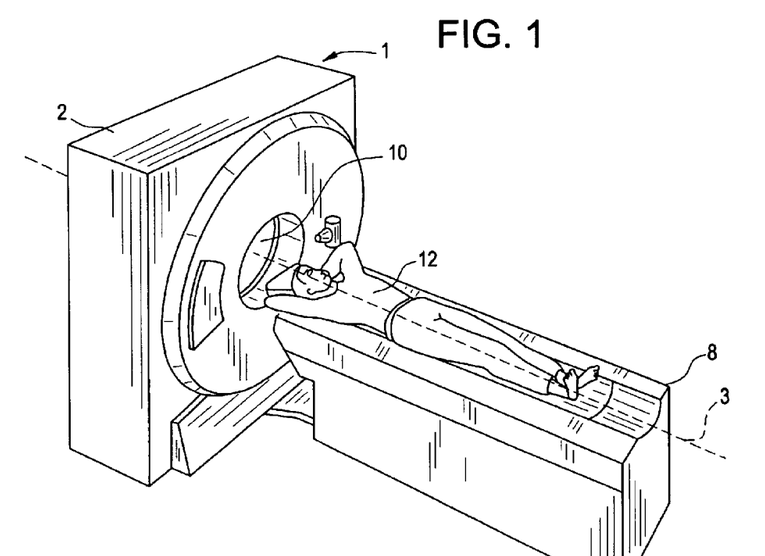
FIG. 1 shows an exemplary CT imaging system and a patient disposed for imaging.
Figure 2:
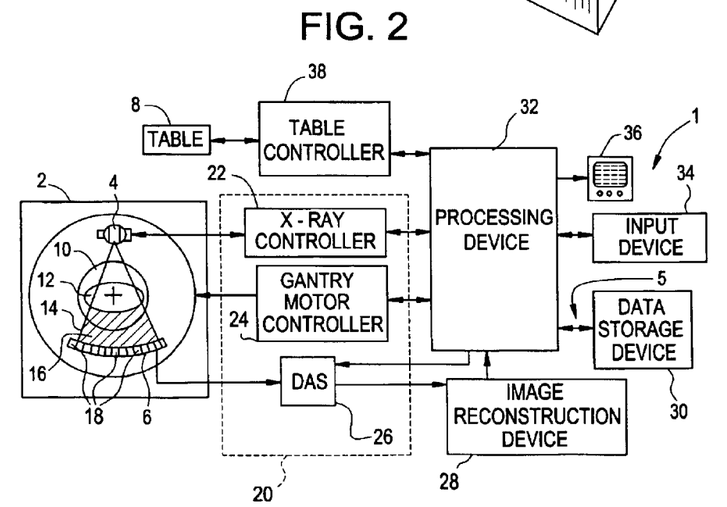
FIG. 2 is a block schematic diagram of an exemplary CT imaging system.
Figure 3:
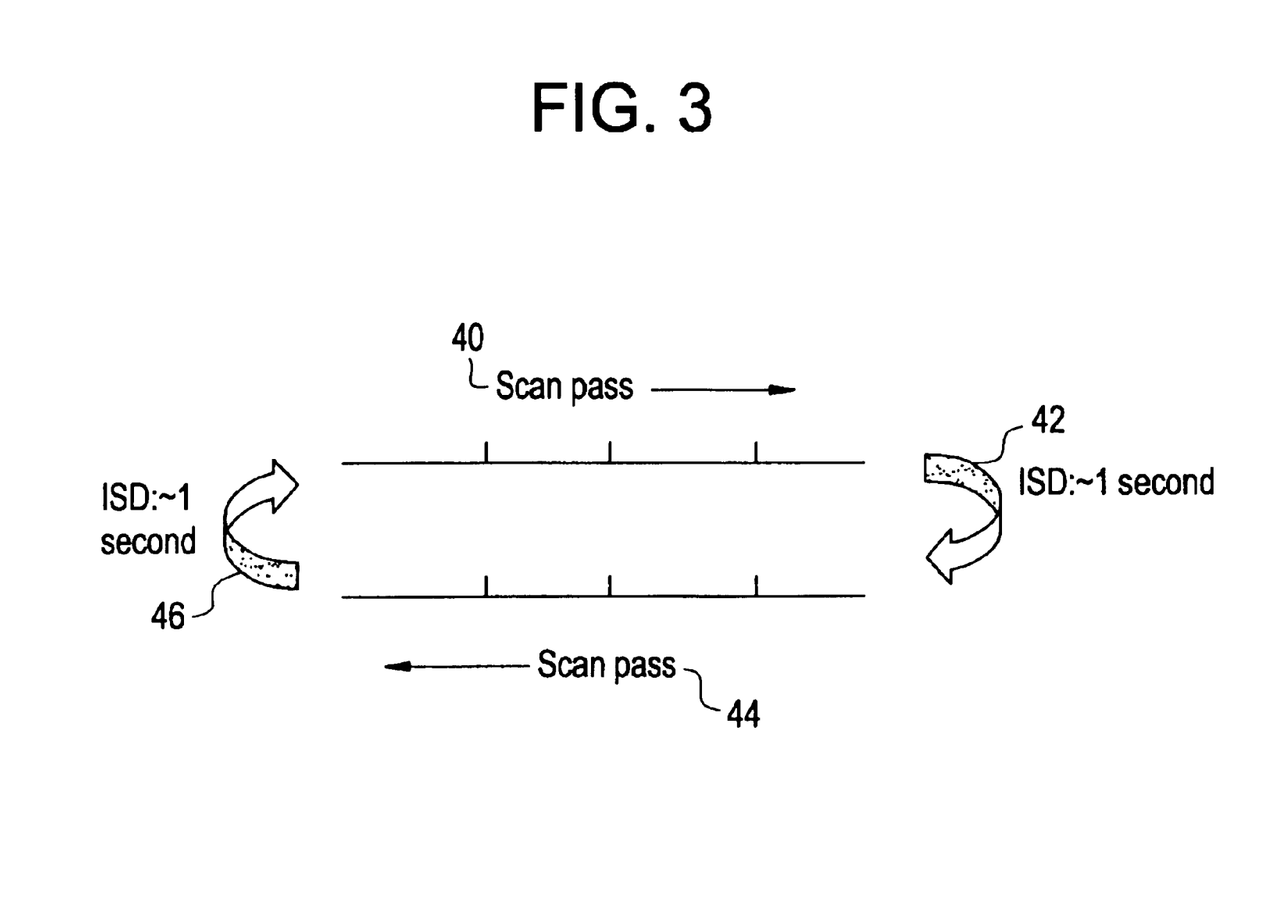
FIG. 3 shows scan coverage for an exemplary CT system.

Referring to FIG. 1 and FIG. 2, an exemplary CT imaging system 1 is shown that includes a gantry 2 having an x-ray source 4, an x-ray detector 6, a patient support structure 8 and a object cavity 10, wherein x-ray source 4 and x-ray detector 6 are opposingly disposed so as to be separated by object cavity 10. An object, such as a patient 12, is disposed upon a displaceable patient support structure 8 ("table"), which is then displaced along an axis 3 extending through object cavity 10. X-ray source 4 projects an x-ray beam 14 toward x-ray detector 6 so as to pass through patient 12. X-ray beam 14 is collimated by a collimate so as to lie within an X-Y plane of a Cartesian coordinate system referred to as an "imaging plane". After passing through and becoming attenuated by patient 12, attenuated x-ray beam 16 is received by x-ray detector 6. X-ray detector 6 includes a plurality of detector elements 18 wherein each of said detector elements 18 receives attenuated x-ray beam 16 and produces an electrical signal responsive to the intensity of attenuated x-ray beam 16.

In addition, x-ray source 4 and x-ray detector 6 are rotatingly disposed relative to gantry 2 and patient support structure 8, so as to allow x-ray source 4 and x-ray detector 6 to rotate around patient support structure 8 when patient support structure 8 is disposed within object cavity 10. X-ray projection data is obtained by rotating x-ray source 4 and x-ray detector 6 around patient 10 during a scan. Helical x-ray projection data is obtained by additionally displacing patient 8 along an axis 3. X-ray source 4 and x-ray detector 6 communicate with a control mechanism 20 associated with CT imaging system 1. Control mechanism 20 controls the rotation and operation of x-ray source 4 and x-ray detector 6.

Control mechanism 20 includes an x-ray controller 22 communicating with x-ray source 4, a gantry motor controller 24, and a data acquisition system ("DAS") 26. DAS 26 communicates with x-ray detector 6. X-ray controller 22 provides power and timing signals to x-ray source 4, gantry motor controller 24 controls the rotational speed and angular position of x-ray source 4 and DAS 26 receives the electrical signals produced by detector elements 18 and converts the signals into data signals for subsequent processing. CT imaging system 1 includes an image reconstruction device 28, a data storage device 30 and a processing device 32, wherein processing device 32 communicates with image reconstruction device 28, gantry motor controller 24, x-ray controller 22, data storage device 30, input device 34 and output device 36. Data storage device 30 comprises any computer usable storage medium known to one of ordinary skill in the art and is in communication with processing device 32 via a propagated signal 5. CT imaging system 1 also includes a table controller 38 communicated with processing device 32 and patient support structure 8, so as to control the position of patient support structure 8 relative to object cavity 10.

Patient 12 is preferably disposed on patient support structure 8, which is then positioned by an operator via processing device 32 so as to be displaceable within object cavity 10. Gantry motor controller 24 is operated via processing device 32 so as to cause x-ray source 4 and x-ray detector 6 to rotate relative to patient 12. X-ray controller 22 is operated via processing device 32 so as to cause x-ray source 4 to emit and project a collimated x-ray beam 14 toward x-ray detector 6 and hence toward patient 12. X-ray beam 14 passes through patient 12 so as to create an attenuated x-ray beam 16, which is received by x-ray detector 6.

Detector elements 18 receive attenuated x-ray beam 16, produce electrical signals responsive to the intensity of attenuated x-ray beam 16 and propagates this electrical signal data to DAS 26. DAS 26 then converts the electrical signals to data signals and communicates the data signals to image reconstruction device 28. Image reconstruction devices perform high-speed image reconstruction. Reconstructed images 32, are stored in data storage device 30 and are displayed via output device 36.

For perfusion and other contrast enhanced exams, the scan must be completed as quickly as possible for a given sampling frequency to maintain enhancement levels while minimizing contrast administered to the patient. Measurements made from contrast bolus tracking are obtained through dynamic scanning (i.e. a time series of images at given locations). The term bolus refers to the amount of contrast injected. Contrast bolus tracking is method for monitoring an injection of contrast in a given region of anatomy. A patient is venously injected with contrast, usually in an extremity, scans are then taken in the anatomy of interest to monitor the arterial inflow and subsequent venous outflow of this contrast. This is displayed as plot of enhancement versus time. The course of inflow to outflow in a given vessel displays as peaks as the bolus of contrast enters and exits the anatomy. Current scan methods use the cine scan mode to image a particular region of anatomy during the time course of the contrast through the region. Cine scan mode is a scan protocol that includes no table movement and comprises scanning the same region/location for a set period of time. (This scan mode is limited by the size of the CT detector, since there is no table movement).

For regions that require more spatial coverage than is achieved with exemplary 2 cm total multi-detector row coverage, the cine scan must be performed at multiple table locations. A generally accepted solution to this is to move the table 8 to the second location as a second exam. For example, the first contrast bolus is monitored at one location. Then the table 8 is moved to the second location, a second contrast injection is administered to the patient 12 and subsequently monitored at this location. This method includes a ten-minute delay between contrast injections, as well as doubling the contrast dose administered to the patient 12. Alternatively, the table 8 may be toggled back and forth between cine locations during one contrast injection. Given that images should be acquired at each location no more than two seconds apart for quality results, the speed limitations of the table 8 restrict the use of this method. For imaging systems 1 including multi-detector row CT scanners, a rapid method to acquire time course images series over relatively large scan areas is desired.

Electron Beam ("EBCT") scanning is achieved by focusing an electron beam at one to four target rings located beneath the patient 12. These targets have gaps between them, thus current scan protocols optimized for maximum spatial coverage contain gaps in this coverage. In an exemplary EBCT scanner, four targets are used to cover up to 7 cm without moving the patient table 8. The targets can each produce 2–7 mm images, and the gaps between targets is 4 mm. Thus, 7 cm of coverage is achieved, but there is 4 mm is missed between each 14 mm of coverage. An efficient method for covering these gaps for a complete axial scan is desired. Moreover, there are also instances where greater total coverage is desired, even if this results in gaps in the data. For systems including EBCT systems, a method for expanding scan coverage area is desired.

Functional maps are the output of the perfusion application and comprise quantitative representations of functional information about the tissue in the anatomy scanned. Examples of functional maps that can be obtained through contrast bolus tracking/dynamic scanning include blood flow, blood volume, and mean transit time. A functional map is computed by acquiring time course images, that is, acquiring approximately one image per second for a set period of time. An exemplary detector configuration for an embodiment of the present invention is a 4×5 mm configuration that is taking 4 slices of the 20 mm detector currently available. Monitoring the contrast enhancement over time in these images provides the data to compute functional parameters for a given spatial location.

A first embodiment of the present invention includes a system and method for helical bi-directional scanning. Bi-directional scanning includes the acquisition of data during both back and forth ("superior to inferior/inferior to superior") displacements of the x-ray detector 6 and/or the object being imaged for purposes including obtaining data for the generation of additional images. A first displacement ("first pass") 40 is followed by an inter-scan delay 42 and a second displacement ("second pass") 44. An inter-scan delay 42, 46 is caused when the x-ray detector 6 and/or the object being imaged decelerate (during a first pass) to a stopped position relative to one another and then accelerate (during a second pass) from the stopped position. An embodiment of the present invention reduces inter-scan delay using scan constraint and scan protocol modifications. Scan constraint and scan protocol modifications include, but are not limited to, the determination of pitch (defined as number of detector lengths covered in one rotation of the gantry 12 in helical/spiral scanning), varying table speed (in mm/s), and eliminating the buffer built in to current scan prescription software constraints. Additionally, setting the starting view angle for the spiral scan to any angle also reduces scan delay. Data acquired from the second pass is utilized for generating additional time point images. Image data is obtained at multiple locations during each pass, with the number of passes being determined for the amount of time coverage required per location. Where images over time are required for a given exam, first and second passes 40, 44 are repeated as necessary. Once complete, the exam contains images over time for the given scan locations.

In one embodiment of the present invention, the structure ("table") 8 utilized to position the object being imaged by a multi-detector row CT scanner is displaced (relative to the x-ray detector) at varying speeds during helical acquisition. It is understood that the present invention may be implemented using any CT scanner and is not limited to multi-row or EBCT scanners. By varying the table speed according to the location being acquired, the table speed during the middle of the acquisition is optimized for scan protocols and the table speed near the start and end of an acquisition pass is optimized for minimal inter-scan delay by using the acceleration periods to acquire data, thus increasing the scan range. As a result, there is an increase in the scan range for a given scan time, because data is acquired during the acceleration and deceleration portions of the helical scan when compared to a system that acquires data only during the time that the table 8 is moving at constant speed.

In another embodiment of the present invention, filament current modulation is employed for extending scan coverage range. Filament current modulation is the varying of the filament current of the x-ray tube used for acquiring CT images. This subsequently affects the number of available electrons to be used in creating an image. Filament current modulation may also be used to maintain total flux in each acquired image slice. Flux is the rate of transfer of the x-rays across the scan region. In one embodiment, current flux is maintained across table speeds by varying x-ray source current. In one example, current modulation may be achieved by adjusting the current of the x-ray source 4 (e.g., tube) to an extent that is proportionate to the table speed thereby causing the x-ray flux obtained for each rotation to remain constant. Alternatively, the x-ray source filament current may be adjusted such that the standard deviation of attenuation in the reconstructed images is uniform across different slices. Standard deviation of the attenuation refers to noise in the image. By placing a defined region of interest on an image, the average and standard deviation values for the attenuation (measured in CT number or Hounsfield units) in a given image can be measured. The standard deviation value is said to be equal to the noise in the image. Therefore, maintaining constant noise across images would be exemplary criteria used for determining the extent of current modulation necessary.

In yet another embodiment, where complete coverage of an object is desired, such as for an EBCT scanner, the gaps between scan areas during a first pass of a scan region are covered during the second pass. In one example, this may be achieved by displacing the table 8 such that gaps not aligned with a detector during a first pass are so aligned with a detector during a subsequent pass. In addition, the inter-scan delay is reduced, to one second for example, as described previously.

Figure 4:
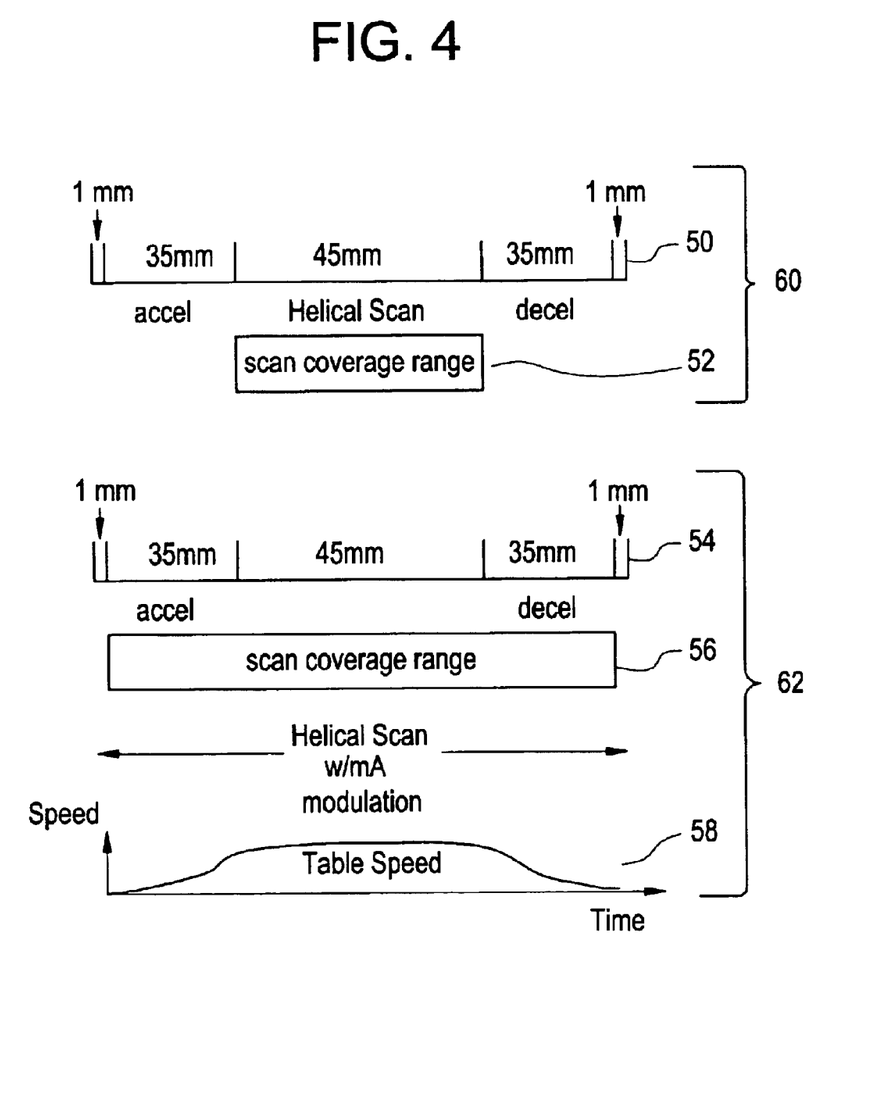
FIG. 4 shows scan coverage for two exemplary multi-detector row CT systems.

FIG. 4 shows scan coverage for two exemplary multi-detector row CT systems in accordance with an exemplary embodiment. The first system 60 comprises a CT system with a 115 mm x-ray total coverage range 50 and a helical scan coverage range 52 of 45 mm, wherein the helical scan coverage range is adjacent two object acceleration/deceleration ranges of 35 mm each. The second system 62 comprises an exemplary CT system enabled with bi-directional helical scanning variable table speed, and current modulation functionality. The variable table speed and current modulation functions cause the second system's scan coverage range 56 to increase (e.g., 115 mm) by providing for data acquisition during periods of acceleration and deceleration. The variable table speed function 58 is determined by and implemented as a function of table position and/or scan coverage range.

Figure 5:
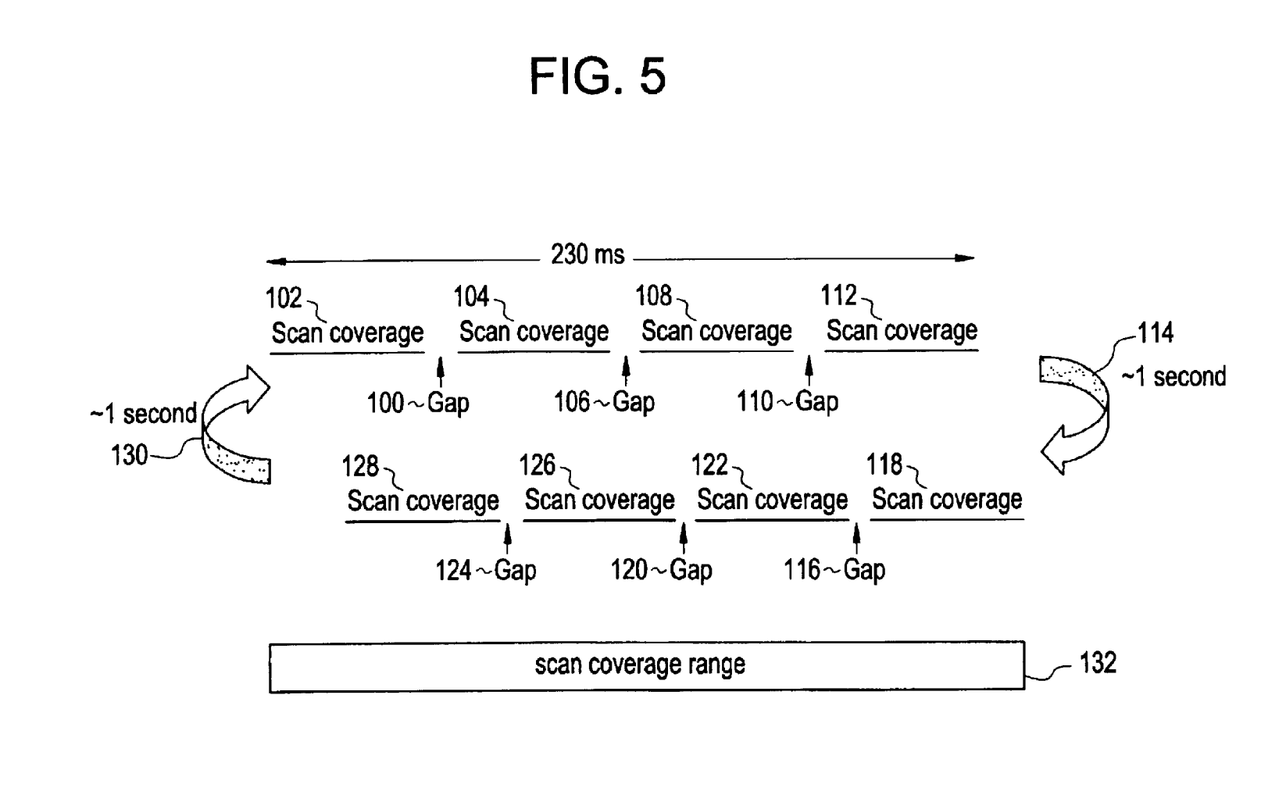
FIG. 5 shows scan coverage for an exemplary electron beam CT system enabled for no-gap scan coverage.

An embodiment of the present invention provides for complete imaging of a scan area wherein no image gaps remain upon scan completion. An image gap comprises a non-imaged area adjacent to at least one imaged areas. For example, an EBCT system may include 4 electron beam targets. The spatial area between targets are generally not imaged and thus result in image gaps. FIG. 5 shows scan coverage 132 for an exemplary electron beam CT system enabled for no-gap scan coverage in accordance with an exemplary embodiment. A first pass results in scan coverage for areas 102, 104, 108, and 112. A second pass (in the opposite direction) results in scan coverage for areas 118, 122, 126, and 128. First pass gaps 100, 106, and 110 are scanned during the second pass. Similarly, second pass gaps 116, 120, and 124 were previously scanned during the first pass. Inter-scan delays 114 and 130 are reduced to the minimum time possible as determined by the physical thresholds of the EBCT system. No gap coverage is achieved using bi-directional scanning and variable table speeds.

Figure 6:
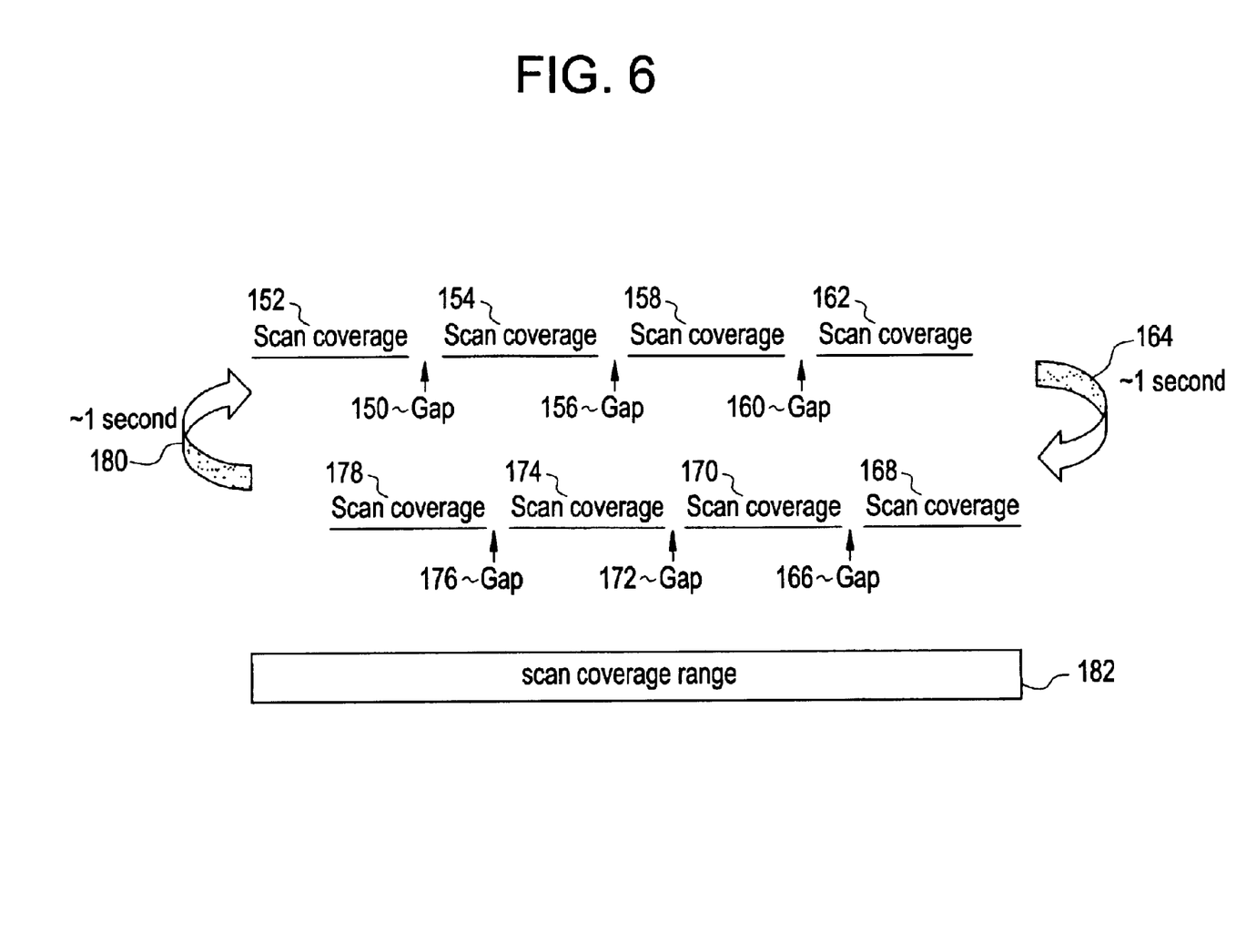
FIG. 6 shows scan coverage for an exemplary electron beam CT system enabled for gapped extended-scan coverage.

Alternatively, for exams where complete (e.g., no gap) imaging is not required, another embodiment provides for an extended maximum coverage range (axial coverage). For example, where an exam does not require total coverage, gaps are not scanned during subsequent passes, and instead an embodiment of the present invention provides for increasing total axial coverage. In this case, the distance the table moves is greater than the detector coverage distance. Referring to FIG. 6, scan coverage 182 with elected gaps for an EBCT system enabled with bi-directional scanning and variable table speed functions is shown. A first pass results in scan coverage for areas 152, 154, 158, and 162. A second pass (in the opposite direction) results in scan coverage for areas 168, 170, 174, and 178. First pass gaps 150, 156, and 160 as well as second pass gaps 166, 172, and 176 are purposefully left un-imaged. The object to be imaged (not shown) is at least partially displaced such that image data for additional scan coverage area 168 may be acquired during the second pass. Inter-scan delays 164 and 180 are reduced to the minimum time possible in accordance with previously described embodiments. Coverage for end areas (shown at 152 and 168 for example) is achieved using variable table speeds thus allowing for data acquisition during periods of acceleration and deceleration.

An embodiment of the present invention may be implemented as new or updated firmware and/or scan prescription functions (i.e. scan and/or reconstruction parameters). Firmware functions include, but are not limited to a more precise table control system that improves the accuracy of table movement, as well as reducing the amount of time required for the table 8 to slow down, stop, and start up in the opposite direction. Scan prescription functions include but are not limited to the following: parameter settings such as table speed, pitch, rotation speed, collimation, start angle for the spiral scan, and constant gantry rotation speed. Scan prescription functions also include reducing or eliminating the pause (buffer time) between deceleration during a first pass and acceleration during a second pass. Firmware and scan prescription functions may be implemented in hardware, software, or a combination thereof. Thus a distinct advantage of the present invention is that it may be implemented for use with existing and/or new CT imaging system 1 or other imaging systems.

Figure 7:
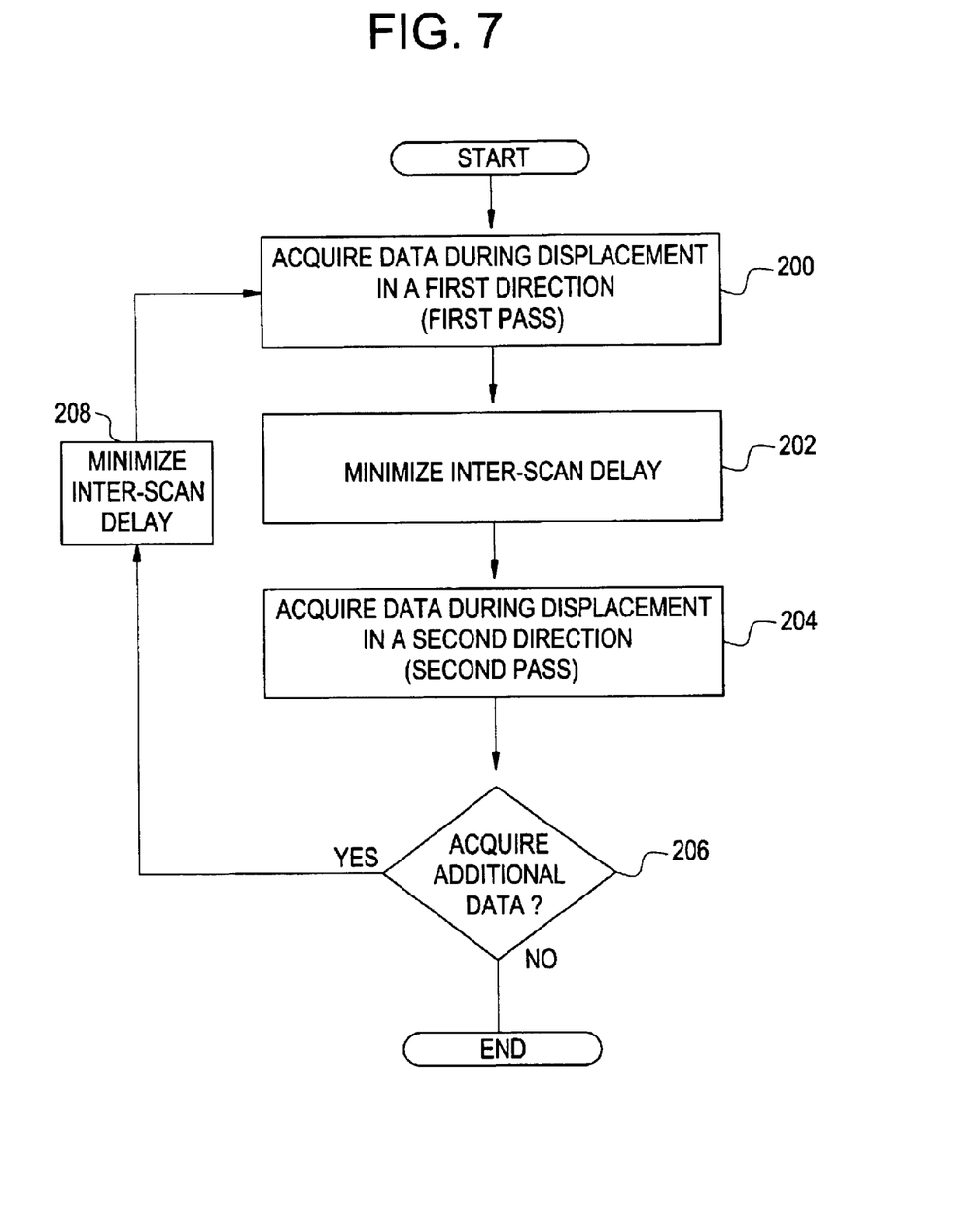
FIG. 7 shows exemplary steps for performing helical bi-directional scanning.
Figure 8:
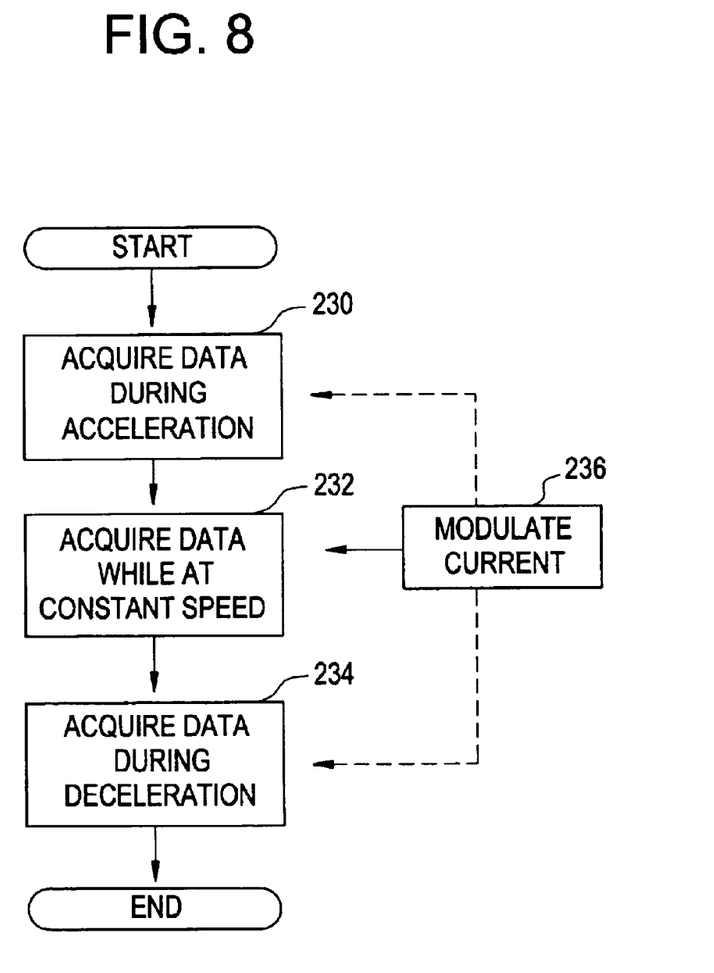
FIG. 8 shows additional steps for performing helical bi-directional scanning.

FIGS. 7 and 8 show a flow chart and a detailed flowchart of exemplary steps for acquiring x-ray image data. It is understood that several embodiments described herein thus far are applicable to and may be implemented in combination with the steps of FIGS. 7 and 8 without exceeding the scope of the present disclosure.

Referring now to FIG. 7, exemplary steps for performing helical bi-directional scanning are shown. Image data is acquired during displacement in a first direction (e.g., first pass) of the x-ray detector 6 and/or object-being imaged at 200. Inter-scan delay is minimized at 202. Image data is acquired during displacement in a second direction (e.g., second pass) of the x-ray detector 6 and/or object being imaged at 204. If coverage over time (acquisition of additional data) is desired at 206, the inter-scan delay is minimized at 208 and then the helical bi-directional scanning process of steps 200 to 204 are iteratively repeated.

FIG. 8 shows additional detail for exemplary steps 200 and/or 204 of FIG. 7. Data is acquired during acceleration at 230, while at constant speed (i.e. center of scan area) at 232, and during deceleration at 234 of the x-ray detector 6 and/or object being imaged. The filament current is modulated at 236 as necessary to facilitate data acquisition during acceleration at 230 and deceleration at 234.

Although the preceding embodiments are discussed with respect to medical imaging, it is understood that the image acquisition and processing methodology described herein is not limited to medical applications, but may be utilized in non-medical applications.

The description applying the above embodiments is merely illustrative. As described above, embodiments in the form of computer-implemented processes and apparatuses for practicing those processes may be included. Also included may be embodiments in the form of computer program code containing instructions embodied in tangible storage media 30, such as floppy diskettes, CD-ROMs, hard drives, or any other computer-readable storage medium, wherein, when the computer program code is loaded into and executed by a computer, the computer becomes an apparatus for practicing the invention. Also included may be embodiments in the form of computer program code, for example, whether stored in a storage medium, loaded into and/or executed by a computer, or as a propagated data signal 5 transmitted, whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the appended claims.

What is claimed is:

1. A method of acquiring x-ray data, comprising:
   acquiring a series of x-ray data for generating at least one x-ray image, said data being acquired using an x-ray detector to receive x-ray beams from an x-ray source, said x-ray source and said x-ray detector being opposingly located relative to one another and being rotatingly disposed relative to an object being imaged, wherein said object is displaced along an axis, said axis extending perpendicularly through a plane defined by said x-ray beams, further wherein said displacement occurs at, at least one of a constant, accelerating, and decelerating rates;
   varying said rate of displacement, said variation enabling said x-ray detector to acquire data for at least one x-ray image during said accelerating or said decelerating displacement; and
   employing current modulation during said acquisition.

2. A method as in claim 1 wherein said object is displaced as follows:
   in a first direction along said axis or
   in a second direction along said axis.

3. A method as in claim 2 wherein said first direction and said second direction are opposite directions relative to one another.

4. A method as in claim 2 wherein data acquired during displacement in said first direction comprises data for at least one image of a first spatial area of said object and data acquired during displacement in said second direction comprises data for at least one image of a second spatial area of said object.

5. A method as in claim 4 wherein said x-ray detector acquires image data for each said first spatial area during a first displacement in one of said directions and said x-ray detector acquires image data for each said second spatial area during a second displacement in the other of said directions.

6. A method as in claim 1, wherein said current modulation further comprises at least one of the following:
   adjusting an x-ray tube current of said x-ray source, said adjustment being proportionate to said rate of displacement to cause an x-ray flux to remain substantially constant, and
   adjusting an x-ray tube current of said x-ray source, said adjustment causing a uniform standard deviation across said generated images.

7. A system for acquiring x-ray data, comprising:
   an x-ray detector for receiving x-ray beams from an x-ray source, said x-ray source and said x-ray detector being opposingly located relative to one another and being rotatingly disposed relative to an object on a support being imaged, said object being displaced along an axis, said axis extending perpendicularly through a plane defined by said x-ray beams, wherein a series of x-ray data for generating at least one x-ray image is acquired by said x-ray detector during said displacement, said displacement occurring at, at least one of a constant, accelerating, and decelerating rates;
   said support having a varying said rate of displacement, said variation enabling said x-ray detector to acquire data for at least one x-ray image during said accelerating or said decelerating displacement; and
   a modulator employing current modulation during said acquisition.

8. A system as in claim 7 wherein said object is displaced as follows:
   in a first direction along said axis or
   in a second direction along said axis.

9. A system as in claim 8 wherein said first direction and said second direction are opposite directions relative to one another.

10. A system as in claim 8 wherein data acquired during displacement in said first direction comprises data for at least one image of a first spatial area of said object and data acquired during displacement in said second direction comprises data for at least one image of a second spatial area of said object.

11. A system as in claim 10 wherein said x-ray detector acquires image data for each said first spatial area during a first displacement in one of said directions and said x-ray detector acquires image data for each said second spatial area during a second displacement in the other of said directions.

12. A system as in claim 7, wherein said current modulation further comprises at least one of the following:
   adjusting an x-ray tube current of said x-ray source, said adjustment being proportionate to said rate of displacement to cause an x-ray flux to remain substantially constant, and
   adjusting an x-ray tube current of said x-ray source, said adjustment causing a uniform standard deviation across said generated images.

13. An article of manufacture comprising a computer usable storage medium, said computer usable storage medium including computer readable program code, said computer readable program code for acquiring x-ray data, said computer readable program code further comprising computer readable program code for performing the following:
   acquiring a series of x-ray data for generating at least one x-ray image, said data being acquired using an x-ray detector to receive x-ray beams from an x-ray source, said x-ray source and said x-ray detector being opposingly located relative to one another and being rotatingly disposed relative to an object being imaged, wherein said object is displaced along an axis, said axis extending perpendicularly through a plane defined by said x-ray beams, further wherein said displacement occurs at, at least one of a constant, accelerating, and decelerating rates;
   varying said rate of displacement, said variation enabling said x-ray detector to acquire data for at least one x-ray image during said accelerating or said decelerating displacement; and
   employing current modulation during said acquisition.

14. An article of manufacture as in claim 13 wherein said object is displaced as follows:
   in a first direction along said axis or
   in a second direction along said axis.

15. An article of manufacture as in claim 14 wherein said first direction and said second direction are opposite directions relative to one another.

16. An article of manufacture as in claim 14 wherein data acquired during displacement in said first direction comprises data for at least one image of a first spatial area of said object and data acquired during displacement in said second direction comprises data for at least one image of a second spatial area of said object.

17. An article of manufacture as in claim 16 wherein said x-ray detector acquires image data for each said first spatial area during a first displacement in one of said directions and said x-ray detector acquires image data for each said second spatial area during a second displacement in the other of said directions.

18. An article of manufacture as in claim 13, wherein said current modulation further comprises at least one of the following:
   adjusting an x-ray tube current of said x-ray source, said adjustment being proportionate to said rate of displacement to cause an x-ray flux to remain substantially constant, and
   adjusting an x-ray tube current of said x-ray source, said adjustment causing a uniform standard deviation across said generated images.

19. A computer data signal, said data signal comprising code configured to cause a controller to implement a method for acquiring x-ray data, the method comprising:
   acquiring a series of x-ray data for generating at least one x-ray image, said data being acquired using an x-ray detector to receive x-ray beams from an x-ray source, said x-ray source and said x-ray detector being oppposingly located relative to one another and being rotatingly disposed relative to an object being imaged, wherein said object is displaced along an axis, said axis extending perpendicularly through a plane defined by said x-ray beams, further wherein said displacement occurs at, at least one of a constant, accelerating, and decelerating rates;
   varying said rate of displacement, said variation enabling said x-ray detector to acquire data for at least one x-ray image during said accelerating or said decelerating displacement; and
   employing current modulation during said acquisition.

20. The computer data signal of claim 19 wherein said object is displaced as follows:
   in a first direction along said axis or
   in a second direction along said axis.

21. The computer data signal of claim 20 wherein said first direction and said second direction are opposite directions relative to one another.

22. The computer data signal of in claim 20 wherein data acquired during displacement in said first direction comprises data for at least one image of a first spatial area of said object and data acquired during displacement in said second direction comprises data for at least one image of a second spatial area of said object.

23. The computer data signal of in claim 22 wherein said x-ray detector acquires image data for each said first spatial area during a first displacement in one of said directions and said x-ray detector acquires image data for each said second spatial area during a second displacement in the other of said directions.

24. The computer data signal of claim 19, wherein said current modulation further comprises at least one of the following:
   adjusting an x-ray tube current of said x-ray source, said adjustment being proportionate to said rate of displacement to cause an x-ray flux to remain substantially constant, and
   adjusting an x-ray tube current of said x-ray source, said adjustment causing a uniform standard deviation across said generated images.

25. A system for acquiring x-ray data, comprising:
   means for acquiring a series of x-ray data for generating at least one x-ray image, said data being acquired using an x-ray detector to receive x-ray beams from an x-ray source, said x-ray source and said x-ray detector being opposingly located relative to one another and being rotatingly disposed relative to an object being imaged, wherein said object is displaced along an axis, said axis extending perpendicularly through a plane defined by said x-ray beams, further wherein said displacement occurs at, at least one of a constant, accelerating, and decelerating rates;

means for varying said rate of displacement, said variation enabling said x-ray detector to acquire data for at least one x-ray image during said accelerating or said decelerating displacement; and means for employing current modulation during said acquisition.

* * * * *